(12) United States Patent
Özer

(10) Patent No.: US 9,730,681 B2
(45) Date of Patent: Aug. 15, 2017

(54) SILICON FISTULA PLUG FOR INTESTINAL FISTULA

(71) Applicant: M. Tahir Özer, Ankara (TR)

(72) Inventor: M. Tahir Özer, Ankara (TR)

(*) Notice: Subject to any disclaimer, the term of this patent is extended or adjusted under 35 U.S.C. 154(b) by 589 days.

(21) Appl. No.: 14/382,842

(22) PCT Filed: Mar. 7, 2013

(86) PCT No.: PCT/TR2013/000076
§ 371 (c)(1),
(2) Date: Sep. 4, 2014

(87) PCT Pub. No.: WO2013/133777
PCT Pub. Date: Sep. 12, 2013

(65) Prior Publication Data
US 2015/0012036 A1  Jan. 8, 2015

(30) Foreign Application Priority Data
Mar. 8, 2012  (TR) .................................. 2012/02652

(51) Int. Cl.
*A61B 17/00*   (2006.01)

(52) U.S. Cl.
CPC ...... *A61B 17/0057* (2013.01); *A61B 2017/00592* (2013.01); *A61B 2017/00615* (2013.01); *A61B 2017/00641* (2013.01); *A61B 2017/00964* (2013.01)

(58) Field of Classification Search
CPC ...... A61B 17/0057; A61B 2017/00615; A61B 2017/00641; A61B 2017/00964; A61B 2017/00592; A61B 2017/00575; A61B 2017/00601
See application file for complete search history.

(56) References Cited

U.S. PATENT DOCUMENTS

2009/0234377 A1  9/2009  Mahlin et al.

FOREIGN PATENT DOCUMENTS

| WO | 95/28885 A1 | 11/1995 |
| WO | 2004/012627 A1 | 2/2004 |
| WO | 2010/028300 A1 | 3/2010 |
| WO | 2010/129162 A1 | 11/2010 |

*Primary Examiner* — Katherine M Shi
*Assistant Examiner* — Michael Mendoza
(74) *Attorney, Agent, or Firm* — Crose Law LLC; Bradley D. Crose

(57) ABSTRACT

The present invention is related to an apparatus to close and control the fistula especially in the enteroatmospheric fistulas occurred in surgical patients, characterized in that it comprises a silicon plug (1) that is made of silicon, and has a flexible, flat and circular shape; a2 connection part (2) that is integrated with silicone plug (1) made of same material and connecting the silicon plug to the suspensory band; at the other end of the connection part, a suspensory band (3) made of latex and having flexible circular form; and a bridge part (6) which is connected to the said structures in order to carry thereof, two surfaces of which are covered with thin sponge part (4), which has an easily bendable thickness and softness, and comprises an aluminum part (5) between sponge parts (4) at the center.

Figure 1:
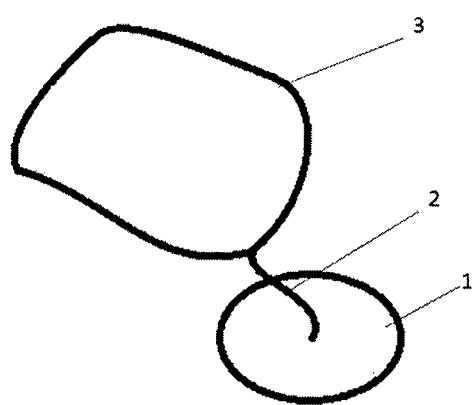
Figure 2:
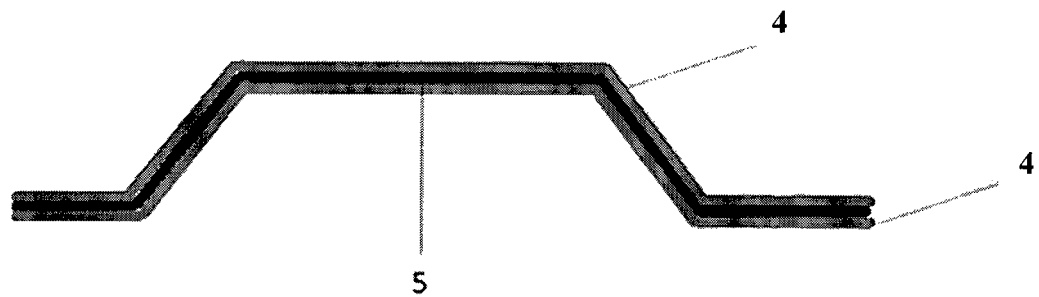
Figure 3:
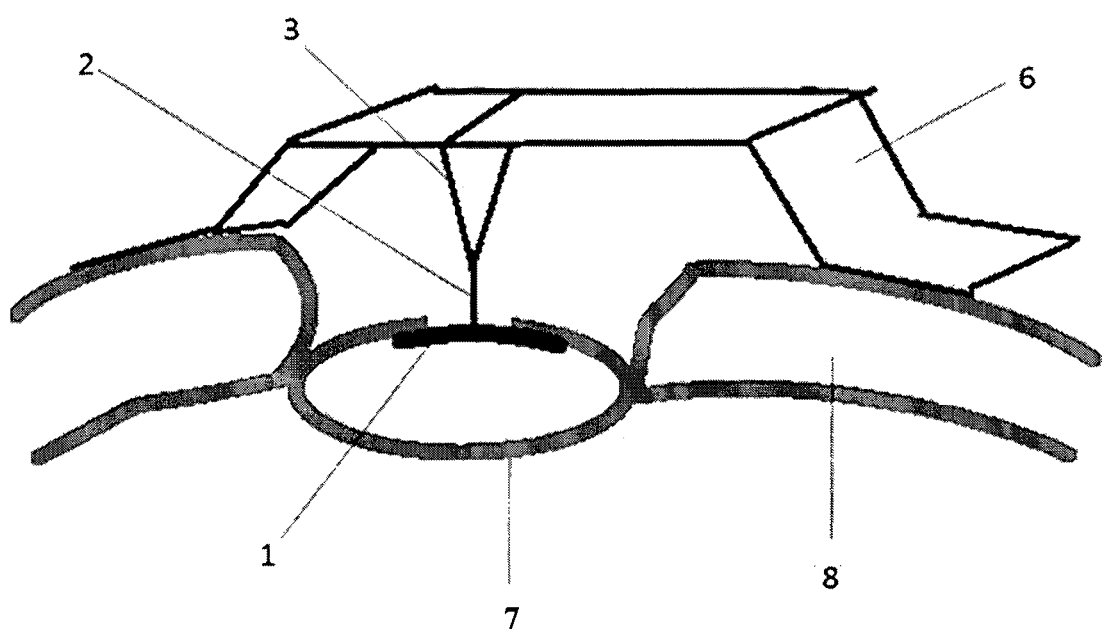

2 Claims, 2 Drawing Sheets

SILICON FISTULA PLUG FOR INTESTINAL FISTULA

RELATED APPLICATION INFORMATION

This application is a 371 of International Application PCT/TR2013/000076 filed 7 Mar. 2013 entitled "Silicon Fistula Plug for Intestinal Fistula", which was published in the English language on 12 Sep. 2013 with International Publication Number WO 2013/133777 A2 and which claims priority from Turkey Patent Application 2012/02652, filed 8 Mar. 2012, the content of which is incorporated herein by reference.

The present invention is related to an apparatus to close and control the fistula especially in the enteroatmospheric fistulas occurred in surgical patients.

In the surgical branches, fistulas developed as a result of both natural course of disease and complication, and these fistulas result in several mortalities and morbidities in the complications they cause. Fluid-electrolyte disturbances may occur in accordance with the level and mass of fistula, and skin burns may occur depending on the corrosive effect of fistula content. In addition, while peritonitis develops, because fistula content in the enteroatmospheric fistulas associated with open abdomen contaminates the intraabdominal area, the auto digestion of the structures such as intraabdominal organs, adipose tissues, connective tissues and supportive tissues may emerge, in other words they may be digested and damaged. This situation results in intractable and severe diseases.

If the fistula forms in any part at abdominal wall, fistula bag and protective creams at least prevent auto digestion. However, applying fistula bag, controlling the content and preventing auto digestion and contamination are not possible in enteroatmospheric fistulas, wherein the fistula forms intra-abdominally in association with open abdomen. Repairs by means of primary sutures to close the fistula cause more growth of the hole in the intestine instead of closing thereof. In order to close the fistula, fistula is removed by means of a critical surgical resection of fistula, end-to-end anastomosis again and ostomy. However, such kind of surgery may not be possible in complicated cases; when the patient does not endure another surgical operation; or if severe intraabdominal adhesions and brids develop. In cases when a surgical operation is not possible in earlier stage, waiting for a length of period to save time for achieving conditions required for controlling the fistula, and surgery, is inevitable.

The object of the present invention is to save time in order to remove the fistula mass by closing the intestine from its inner surface by means of silicone plug developed, form barriers in association with the defense mechanisms of the body in the meantime, provide the peritonization of the intestines in the anterior open part of the abdomen, and to heal this peritonized area by making it smaller thanks to granulation, and to close the fistula via granulation or at least, to control the contamination by cutting the fistula flow by means of silicon plug, and to gain time which provides the opportunity to provide the conditions to apply main surgical treatment.

1. DESCRIPTION OF THE FIGURES

1. The view of internal fistula plug
2. The view of the bridge to which internal fistula plug is suspended, shaped in accordance with the status and anatomy of the patient.
3. The view of internal fistula plug applied to the patient and suspended to the bridge.

2. DESCRIPTION OF THE PARTS

1. Silicon plug
2. Connection part
3. Suspensory band
4. Sponge part
5. Aluminum part
6. Bridge part
7. Intestine
8. Anterior abdominal wall The silicon plug (1) according to the invention is made of silicon and it has flat and circular and flexible form. It comprises a connection part (2) that is integrated with this part, made of same material and connecting the silicon plug to the band, and a suspensory band (3) made of latex and having flexible and circular form, is provided at the other end of the connection part. Also, in order to carry the said described structure by suspending, the apparatus includes a bridge part (6), two surfaces of which are covered with thin sponge part (4), which has easily flexible thickness and softness, comprises an aluminum part (5) at the center, as a separate carrier part. The said bridge part (6) is shaped and placed in front of open anterior abdominal wall (8) of the patient and fistula orifice in the intestine is closed internally by suspending the silicon plug upwards.

The silicon plug (1) according to the invention is pushed into the intestine from the hole of the fistulous intestine (7) by being rolled thanks to the flexibility of the silicon, and after it penetrates into intestine, it expands and takes a circular shape thanks to its flexibility. Silicon intermediate connection part (2) integrated with silicon plug and flexible latex suspensory band (3) connected thereof are left outside. The said part is suspended to the part that is made of sponge and aluminum (4, 5) and implanted to the anterior abdominal wall (8) by being given a bridge form (6) via a flexible latex suspensory band (3), and thus, it is provided that the fistula is closed internally and the flow is cut by implanting the silicon plug (1) to the intestine mucous membrane.

The invention claimed is:
1. An apparatus for plugging a fistulous opening in a wall of an abdominal cavity, the apparatus comprising:
   (a) a flexible bridge comprising a middle portion and opposed first and second end portions, wherein the bridge is shapeable to enable the first and second end portions of the bridge to be placed in contact with respective external surfaces of the wall on opposite sides of the fistulous opening with the bridge spanning the fistulous opening,
   (b) a flexible plug having an expanded form that enables the flexible plug to cover the fistulous opening, the flexible plug being foldable to a form that allows the flexible plug to penetrate through the fistulous opening into the abdominal cavity where the flexible plug can expand and return to the expanded form; and
   (c) means for suspending the flexible plug from the middle portion of the bridge with the bridge capable of spanning the fistulous opening and with the flexible plug in the abdominal cavity in expanded form and covering the fistulous opening, wherein the means for suspending comprises a band configured for encircling the middle portion of the bridge and an elongate connection part having a first end connected to the flexible plug and a second end connected to the band, wherein the flexible plug is made of silicon, wherein the flexible plug is flat and circular in the expanded form, wherein the connection part is integrally formed with the flexible plug, wherein the bridge comprises first and second spongy surfaces sandwiching a middle surface comprising aluminum, and wherein the band is made of latex and has a circular form.

2. A method for plugging a fistulous opening in a wall of an abdominal cavity, the method comprising the steps of:
   (a) providing the apparatus of claim 1,
   (b) folding the flexible plug and inserting it through the fistulous opening into the abdominal cavity, without also inserting into the abdominal cavity the connection part and the band, and allowing the inserted flexible plug to expand to the expanded form within the abdominal cavity, the connection part and the band remaining outside of the abdominal cavity;
   (c) suspending the inserted flexible plug from the bridge with the flexible plug covering the fistulous opening by positioning the band around the middle portion of the bridge and shaping and placing the first and second end portions of the bridge in contact with respective external surfaces of the wall on opposite sides of the fistulous opening with the bridge spanning the fistulous opening.

* * * * *